United States Patent [19]

Bezwada et al.

[11] Patent Number: 5,147,383
[45] Date of Patent: Sep. 15, 1992

[54] SUTURE COATED WITH A POLYVINYL ESTER

[75] Inventors: Rao S. Bezwada, Whitehouse Station; Alastair W. Hunter, Bridgewater, both of N.J.

[73] Assignee: Ethicon, Inc., Somerville, N.J.

[21] Appl. No.: 792,321

[22] Filed: Nov. 12, 1991

Related U.S. Application Data

[62] Division of Ser. No. 473,505, Feb. 1, 1990, Pat. No. 5,089,013.

[51] Int. Cl.$^5$ .............................................. A61L 17/00
[52] U.S. Cl. ..................................... 606/231; 606/228
[58] Field of Search ....................... 606/228, 231, 230

[56] References Cited

U.S. PATENT DOCUMENTS

| 2,072,303 | 3/1937 | Herrmann et al. | 606/231 |
| 3,942,532 | 3/1976 | Hunter et al. | 606/231 |
| 4,027,676 | 6/1977 | Mattei | 606/231 X |
| 4,124,748 | 11/1978 | Fujimoto et al. | 604/368 X |
| 4,185,637 | 1/1980 | Mattei | 606/230 |
| 4,201,216 | 5/1980 | Mattei | 606/231 X |
| 4,693,939 | 9/1987 | Ofstead | 623/5 X |
| 4,844,067 | 7/1989 | Ikada et al. | 606/231 |
| 4,983,180 | 1/1991 | Kawai et al. | 606/231 X |

Primary Examiner—Stephen C. Pellegrino
Assistant Examiner—Jeffrey A. Schmidt
Attorney, Agent, or Firm—Matthew S. Goodwin

[57] ABSTRACT

A surgical suture having a coating thereon of at least one polyvinyl ester, and a method for improving the knot tiedown performance of a suture by first coating a polyvinyl ester solution onto the surface of the suture and then removing the solvent from the coated suture.

11 Claims, No Drawings

SUTURE COATED WITH A POLYVINYL ESTER

This is a division of application Ser. No. 473,505, filed Feb. 1, 1990, U.S. Pat. No. 5,089,013.

BACKGROUND OF THE INVENTION

This invention relates to coated surgical sutures. More specifically, it relates to sutures coated with a vinyl polymer and to a method for improving the knot tiedown performance of a surgical suture.

Surgical sutures often require a surface coating to improve one or more of their performance properties. For example, a multifilament suture typically requires a surface coating to improve the tactile smoothness, pliability and tiedown Performance of the suture, so it passes easily and smoothly through tissue during operative procedures. A monofilament suture may also require a surface coating to reduce the stiff feel of the suture and to increase its pliability.

In response to the need for suitable coatings for surgical sutures, numerous patents have disclosed potential coating compositions. U.S. Pat. No. 3,942,532 discloses a polyester coating for multifilament sutures. The preferred polyester coating is polybutilate, which is the condensation product of 1,4-butanediol and adipic acid. U.S. Pat. No. 4,105,034 discloses a multifilament suture coating of a poly(alkylene oxalate), e.g. poly(hexamethylene oxalate). Although the coating compositions disclosed in these patents exhibit excellent handling characteristics and enhance many of the properties of the coated suture, the knot integrity of the coated suture diminishes slightly.

U.S. Pat. No. 3,527,650 discloses a coating of polytetrafluoroethylene (PTFE) particles in an acrylic latex. Although PTFE acts as an excellent lubricant to decrease the roughness of multifilament sutures, it has a tendency to flake off during use. Also, this particular coating is a thermoset which requires a curing step for proper application. U.S. Pat. No. 4,043,344 discloses a PLURONICS ™ ethylene oxide/propylene oxide copolymer coating for nonabsorbable surgical sutures. Unfortunately, these copolymer coatings lose their lubricity during wet tiedown evaluations.

In view of the deficiencies with the potential candidates for suture coatings, it would be desirable to develop a coating for a suture that can be applied using conventional techniques, that increases the tactile smoothness of the coated suture without sacrificing its physical properties, and that does not adversely affect the knot integrity of the suture.

SUMMARY OF THE INVENTION

In one aspect, the invention is a suture having its surface coated with an amount of at least one polyvinyl ester effective to improve its knot tiedown performance relative to the knot tiedown performance of the uncoated suture.

In another aspect, the invention is a method of improving the knot tiedown performance of a suture. This method comprises the steps of coating the surface of the suture with an effective amount of a solution of at least one polyvinyl ester in an organic solvent, and then removing the solvent from the coated suture.

The polyvinyl ester coating of this invention can be applied to the surface of a suture using conventional techniques. The knot tiedown performance of the coated suture, which is an indication of its tactile smoothness, dramatically improves without sacrificing the tensile properties of the coated suture. Surprisingly, these improvements in properties are acheived without adversely affecting the knot security of the coated suture.

DETAILED DESCRIPTION OF THE INVENTION

Polyvinyl (Pv) esters within the scope of this invention are known and can be prepared by conventional techniques, for example, by polymerizing a vinyl ester monomer using a free radical initiation process. Preferably, the PV ester is represented by repeating units of the formula:

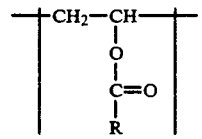

wherein R is $C_{6-30}$ straight or branched alkyl.

If the alkyl group of the formula above were to have less than 10 carbons, then the ester would not typically exhibit good coating properties. If the alkyl group were to have greater than 30 carbons, then the availability and purity of the ester would typically not be desirable for coating applications Preferably, R is $C_{14-18}$ straight alkyl. The most preferred PV ester is polyvinyl stearate.

The amount of PV ester coated onto the surface of the suture to improve knot tiedown performance will generally depend on the molecular weight of the PV ester and can readily be determined empirically. In most instances, the required amount of PV ester decreases as its molecular weight increases. Advantageously, the amount of PV ester coated onto the suture ranges from about 0.3 to about 20, preferably from about 0.5 to about 15 percent of the weight of the coated suture. Generally, amounts greater than 20 weight percent may compromise the knot security of the coated suture and amounts below 0.3 weight percent may fail to achieve any significant improvement in suture properties. The suture can be coated with not only one PV ester, but also a mixture of 2 or more PV esters, if desired. Preferably, the suture is coated with one PV ester.

The PV ester coatings of this invention are typically characterized by a weight average molecular weight as determined by gel permeation chromatography ranging from about 50,000 to about 2,000,000, preferably from about 100,000 to about 1,000,000, and most perferably from about 200,000 to about 500,000. A PV ester with molecular weight below 50,000 may fail to significantly improve the knot tiedown of a coated suture, and a PV ester with molecular weight above 2,000,000 may increase the stiffness of the coated suture.

Sutures within the scope of this invention can be of any type used or contemplated for operative procedures. The suture can be synthetic or natural, absorbable or nonabsorbable, or a monofilament or multifilament in a braided, twisted or covered form. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from polymers of one or more lactones, e.g. VICRYL ® poly(lactide-co-glycolide) multifilament suture. Examples of nonabsorbable monofilament and multifilament sutures include nylon, polypropylene, steel, polyvinylidene fluoride, linen, cotton, silk, and polyesters such as polyethylene terephthalate (PET). The preferred sutures are nonabsorbable, multifilament sutures, preferably polyester sutures. The most preferred suture is PET.

The organic solvent for the PV ester coating of this invention is advantageously a solvent which has a normal boiling point no greater than 120° C. Examples of suitable organic solvents include but are not limited to chlorinated aliphatic solvents such as 1,1,2-trichloroethane and aromatic solvents such as toluene.

The coating can easily be prepared by simply dissolving the PV ester into the appropriate organic solvent. The concentration of the ester in solution will, of course, depend on the amount of PV ester desirably coated onto the surface of the suture, but generally should range from about 3 to about 20, preferably from about 5 to about 15 weight percent.

Once a solution of the PV ester is prepared, a suture can be coated using conventional coating techniques, e.g. dipping, spraying, etc. After the coating is applied, the solvent can be removed by drying in air, or by other techniques well known in the art, for example, removing the solvent at an elevated temperature under vacuum.

The organic solvent and the preparation of a coating solution for application is normally required for coating multifilament sutures. However, an alternative approach is feasible for coating monofilament sutures without requiring the preparation of coating solution. If a synthetic monofilament suture is to be coated, then the fiber-forming polymer from which the suture is derived could be coextruded with a suitably low molecular weight PV ester so that the ester could exude to the surface of the fiber during extrusion to increase its tactile smoothness. Such methods have been demonstrated to enhance the lubricity and knotting characteristics of the fiber-forming polymer.

The PV ester in preferred embodiments of this invention is an essentially nonabsorbable, water insoluble, waxy solid. However, the ester can be modified or additives can be incorporated into the coating composition to tailor coating properties for specific applications. For example, the ester can be made water soluble by copolymerizing the ester with a polyvinyl alcohol and/or polyvinyl pyrrolidone. Alternatively, a vinyl alcohol ester could be copolymerized with vinyl alcohol and/or vinyl pyrrolidone. A bioabsorbable ester especially suited for absorbable sutures can be prepared by first functionalizing a low molecular weight PV ester, and then copolymerizing it with one or more lactones, e.g. glycolide, e-caprolactone, lactide, p-dioxanone, and the like. Similarly, silicone lubricating agents such as polydimethylsiloxane resins and elastomers, as well as other known polymeric coatings such as homopolymers and copolymers of p-dioxanone and PLURONICS TM ethylene oxide/propylene oxide copolymers, can be added to the coating composition to modify or enhance the final properties of the coated suture. All of these embodiments, as well as similar embodiments to modify or enhance the coated suture properties, are well within the scope of the claimed invention.

Although the PV ester has been described as a coating for surgical sutures, noncoating applications can be readily envisioned. For example, the PV ester may be used as a slip agent in thermo-dye transfer processes, as an elastomeric component for polyester molding compounds for bumpers and dashboards of automobiles, as a component in tissue adhesives for dentistry and surgery and as a component in jet printing ink applications.

The following example illustrates but is in no way intended to limit the scope of the claimed invention. In the example, the tensile properties, tiedown roughness and knot security are each determined using an Instron Tensile Tester. The tensile properties, i.e. The straight and knot tensile strength and the percent elongation, are determined generally according to the procedures described in U.S. Pat. No. 4,838,267. The tiedown roughness is a measure of the knot tiedown performance. It provides an indication of the force required to slide a knot down a suture, and it is determined generally according to the procedure described in U.S. Pat. No. 3,942,532. The knot security, which provides an indication as to the number of throws required to secure a knot so that it fails to slip before cleanly breaking, is measured by first tieing a conventional square knot around a mandrel, pulling the knot apart on the Instron Tester to observe whether slipping occurs, and if so, then tieing knots with additional throws until 20 out of 20 knots break cleanly without slipping.

EXAMPLE

For each of three runs, a solution of polyvinyl stearate with a weight average molecular weight of 239,000 and a melting temperature of 48° C. in toluene is prepared. A size 2/0 (USP standard) MERSILENE ® PET braided multifilament suture is coated at room temperature with the coating solution using conventional laboratory coating equipment, and the coated suture is subsequently dried in air at 110° F. to remove the toluene. Table 1 compares the tensile and tiedown roughness properties and the knot security characteristics for each of the three runs with an uncoated MERSILENCE ® PET braided multifilament suture.

TABLE 1

PROPERTIES OF POLYESTER SUTURE COATED WITH POLYVINYL STEARATE (PVS)

| | PVS COATING CONCENTRATION IN TOLUENE, WT. PERCENT | | | UNCOATED SUTURE |
|---|---|---|---|---|
| | 5.15 | 8.10 | 12.15 | CONTROL |
| Percent Solids[1], wt. | 0.97 | 1.74 | 5.20 | — |
| Suture Diameter, mils. | 13.60 | 13.64 | 13.93 | 13.23 |
| Dry Tiedown Roughness, gms. | 140.4 | 127.8 | 118.6 | 355.5 |
| Wet[2] Tiedown Roughness, gms. | 126.2 | 135.4 | 137.1 | 249.2 |
| Wet Knot Security | 4 | 4 | 4 | 4 |
| Dry Knot Tensile Strength, psi | 52,567 | 51,973 | 50,232 | 52,458 |
| Wet Knot Tensile Strength, psi | 53,971 | 54,452 | 48,832 | 56,794 |
| Dry Straight Tensile Strength, psi | 94,882 | 94,235 | 91,994 | 102,946 |
| Percent Elongation | 14.70 | 15.00 | 16.30 | 16.27 |

[1]Determined by measuring the difference in weight between the coated and uncoated suture.
[2]Wet properties are determined after soaking the suture in water at 25° C. for at least 24 hours.

The results indicate that the polyester suture coated with a varying amount of Polyvinyl stearate exhibits significantly improved dry and wet tiedown roughness relative to that of the uncoated suture. The improved roughness is acheived without sacrificing knot security or the tensile properties of the uncoated suture. Generally, a wet tiedown roughness of less than 200 grams, preferably less than 150 grams, for the coated sutures of this invention can be readily obtained.

Similar outstanding results can be obtained with other PV ester coatings within the scope of the claimed invention.

We claim:

1. A suture wherein the outer surface thereof is coated with at least one homopolymer of a vinyl ester monomer in an amount between about 0.3 to about 20 percent of the weight of the coated suture.

2. The suture of claim 1 wherein the surface thereof is coated with one homopolymer of a vinyl ester monomer.

3. The suture of claim 2 wherein the homopolymer is represented by repeating units of the formula:

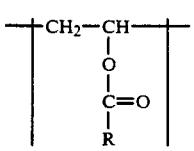

where R is $C_{6-30}$ straight or branched alkyl.

4. The suture of claim 3 wherein R is $C_{14-18}$ straight alkyl.

5. The suture of claim 4 wherein the homopolymer is polyvinyl steasrate.

6. The issue of claim 5 wherein the molecular weight of the homopolymer is between about 200,00 and about 500,000.

7. The suture of claim 6 wherein the he suture is a monofilament or multifilament suture with or without one or more needles.

8. The suture of claim 7 wherein the he suture is a multifilament suture.

9. The suture of claim 8 wherein he multifilament suture is an nonabsorbable suture.

10. The suture of claim 9 wherein the he suture is a polyester.

11. The suture of claim 10 wherein the polyester is polyethylene terephthalate.

* * * * *

UNITED STATES PATENT AND TRADEMARK OFFICE
CERTIFICATE OF CORRECTION

PATENT NO. : 5,147,383
DATED : September 15, 1992
INVENTOR(S) : Rao S. Bezwada and Alastair W. Hunter It is certified that error appears in the above-identified patent and that said Letters Patent is hereby corrected as shown below:

Column 6:

In claim 5 "steasrate" should be -- stearate --.

In claim 6, "issue" should be -- suture --.

In claim 7, "he" should be eliminated.

In claim 8, "he" should be eliminated.

In claim 9, "he" should be -- the --.

In claim 10, "he" should be eliminated.

Signed and Sealed this

Nineteenth Day of October, 1993

Attest:

BRUCE LEHMAN

*Attesting Officer*     Commissioner of Patents and Trademarks